United States Patent [19]

Champonnois et al.

[11] Patent Number: 4,954,778
[45] Date of Patent: Sep. 4, 1990

[54] EDDY CURRENT TESTING SYSTEM USING TWO SAMPLES WITH DIFFERENT TIME LAGS

[75] Inventors: Francois Champonnois, Paris; Bernard David, Gif/Yvette; Francis Joffre, Bures sur Yvette, all of France

[73] Assignee: Commissariat a l'Energie Atomique, Paris, France

[21] Appl. No.: 311,356

[22] Filed: Feb. 16, 1989

[30] Foreign Application Priority Data

Feb. 26, 1988 [FR] France .................. 88 02377

[51] Int. Cl.⁵ .................. G01N 27/90; G01R 33/12
[52] U.S. Cl. .................. 324/233; 324/240
[58] Field of Search .................. 324/232–243, 324/225, 227, 228

[56] References Cited

U.S. PATENT DOCUMENTS

| | | | |
|---|---|---|---|
| 3,197,693 | 7/1965 | Libby | 324/233 X |
| 3,229,197 | 1/1966 | Renken, Jr. | 324/240 |
| 3,229,198 | 1/1966 | Libby | 324/233 |
| 3,895,290 | 7/1975 | Audenard et al. | 324/233 |
| 4,061,968 | 12/1977 | Pigeon | 324/234 |
| 4,084,136 | 4/1978 | Libby et al. | 324/238 |
| 4,109,201 | 8/1978 | Pigeon et al. | 324/227 |
| 4,322,683 | 3/1982 | Vieira et al. | 324/233 X |
| 4,326,166 | 4/1982 | Pigeon et al. | 324/233 X |

FOREIGN PATENT DOCUMENTS 2324003  4/1977  France .................. 324/237

OTHER PUBLICATIONS

G. Whittig et al, "Design of a Pulsed Eddy–Current Test Equipment with Digital Signal Analysis", 1981, pp. 387–397.

Primary Examiner—Gerard R. Strecker
Assistant Examiner—Warren S. Edmonds
Attorney, Agent, or Firm—Oblon, Spivak, McClelland, Maier & Neustadt

[57] ABSTRACT

A pulsed eddy current testing system for detecting defects in a part. A probe carries an exciting pulse in one coil and receives a measuring signal in a second coil. The measuring signal is sampled at two instants defined by short and long time lags. The two amplitudes obtained are plotted in a representative plane having two reference axes. The point having the signals as coordinates describes a figure eight, when the part has a defect. The size and orientation of the figure gives information on the defect in the part.

16 Claims, 7 Drawing Sheets

EDDY CURRENT TESTING SYSTEM USING TWO SAMPLES WITH DIFFERENT TIME LAGS

The present invention relates to a pulsed eddy current control process and to an apparatus for performing the same. The application applies to the non-destructive testing, inspection or control of metal parts, particularly thick and/or ferromagnetic parts.

Eddy current control or inspection apparatuses usually use sinusoidal excitation signals with a given frequency. A description thereof is provided in U.S. Pat. No. 3,229,198, granted on Jan. 11th 1966 to H. L. LIBBY and entitled "Eddy current non-destructive testing device for measuring multiple parameter variable of a metal sample".

In certain improved apparatuses, use is made of several sinusoidal signals at different frequencies, as described in French patent 2 324 003 entitled "Eddy current non-destructive inspection process and apparatus using a multifrequency excitation and permitting the elimination of certain parameters".

In a variant of the multifrequency currents, N square-wave signals of a period which is a submultiple of a period T are superimposed to obtain a recurrent sequency of square-wave pulses of width T/N and recurrence period T. This superimposing leads to the excitation of the probe. As in multifrequency apparatuses, the recurrent measuring signal is analyzed by using N square-wave signals for detecting the components of the period which is a submultiple of the recurrence period.

The use of square-wave signals in place of sinusoidal signals facilitates the digital processing of the signal. It is then possible to make combinations of samples in accordance with various linear transformations known as the Walsh transformation. The result of these complex transformations is displayed and interpreted. This method is described in U.S. Pat. No. 4,084,136 granted to LIBBY et al.

However, the use of periodic signals is not always desirable. This is the case when the part to be inspected is thick and ferromagnetic. Thus, in this case, the high magnetic permeability leads to a significant skin effect, which renders inaccessible the deep areas of the part. Preference is then given to the use of pulsed signals, which lead to a greater instantaneous power making it possible to saturate the ferromagnetic material. The permeability is then greatly decreased and the penetration of the currents is improved.

Such a method is described in U.S. Pat. 3,229,197 and uses two types of pulses, one short and the long. These two types alternate in such a way that the probe delivers alternately long and short pulses. However, a zero measurement signal is obtained if the part is faultless. Any defect or fault unbalances the signal and therefore reveals its existence.

The non-destructive inspection method using pulsed eddy currents closest to the present invention is described in the article by G. WITTIG and H. M. THOMAS entitled "Design of a Pulsed Eddy-Current Test Equipment with Digital Signal Analysis" published in the book Eddy-Current Characterization of Materials and Structures, ASTM STP 722, George Birnbaum and George Free, Eds., American Society for Testing and Materials, 1981, pp 387–397, as well as in the references quoted therein.

Figure 1:
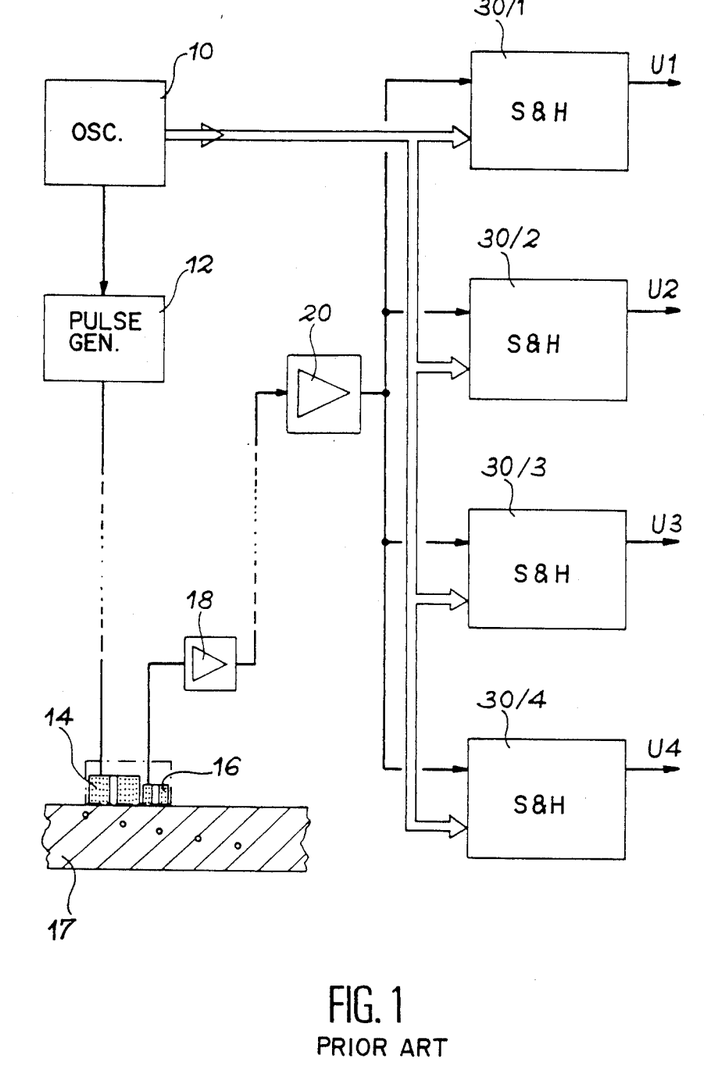
FIG. 1: The structure of a prior art application.

FIG. 1 shows the structure of a prior art apparatus operating according to this principle. This apparatus comprises a stable oscillator 10, e.g. operating at 1 MHz, a pulse generator 12 supplying current pulses, whose duration is dependent on the inductance and capacitance values of the circuit and which is approximately 5 to 75 $\mu$s. The intensity can be about 10 amperes. A probe comprises an exciting winding 14 and a measuring winding 16. The probe moves along a part 17 to be inspected using not shown means. The voltage taken at the terminals of winding 16 is applied to a low noise preamplifier 18, to which is connected an amplifier 20.

In the represented example, the apparatus also comprises four channels 30/1, 30/2, 30/3 and 30/4, whose function is to sample the measuring signal and hold the sample value. The voltages finally supplied by the four channels are designated U1, U2, U3 and U4.

FIG. 2 illustrates the operation of this apparatus: line (a) represents the pulses T supplied by circuit 10, line (b) represents the pulses I supplied by generator 12 and applied to the exciting winding 14 of the probe, line (c) shows the path of the signal Um collected at the terminals of the probe measuring winding 16, line (d) shows the time lag on sampling t1 and the hold time tH for the first channel 30/1, line (e) shows the time lag on sampling t3 and the hold time tH for the third channel 30/3, line (f) shows the voltage U1 supplied by channel 30/1, which characterizes in magnitude and sign the evolution of the sample of the measurinng signal taken at time t1, i.e. Um(t1), finally line (g) shows the voltage U3 supplied by channel 30/3, which characterizes in magnitude and sign the evolution of the sample of the measuring signal taken at time t3, i.e. Um(t3).

Figure 2A:
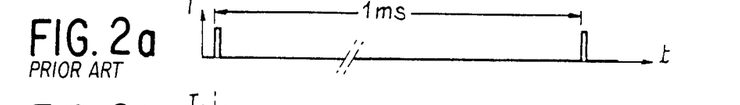
FIGS. 2a–2g: The operation of the prior art apparatus of FIG. 1.
Figure 2B:
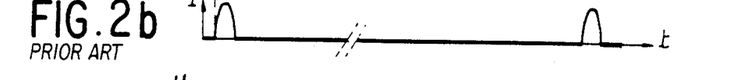
Figures 2C, 2D:
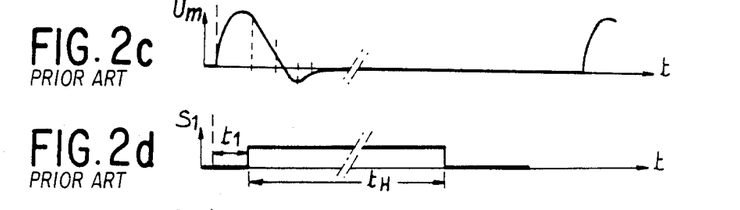
Figure 2E:
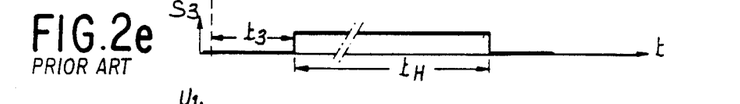
Figure 2F:
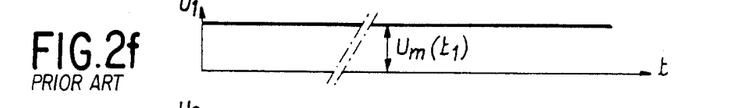
Figure 2G:
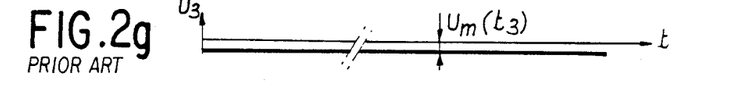

The continuity of signals U1 and U3 is obtained by a low-pass filtering, which smooths the sampled curve.

When the probe travels along the part to be inspected, each voltage supplied by the sample and hold channels varies as a function of the quality of the part and said variations make it possible to control said quality.

Figure 3A:
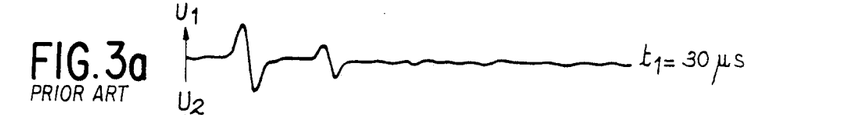
FIGS. 3a–3e: The signal of the four channels shown in FIG. 1.
Figures 3B, 3C, 3D:
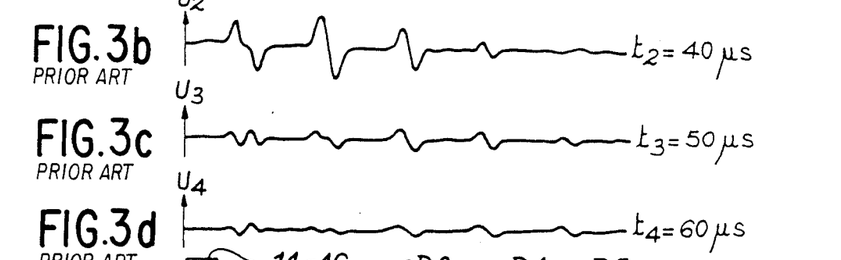

This is shown in FIG. 3, where it is possible to see four lines (a), (b), (c) and (d) corresponding to the variations of the four voltages U1, U2, U3 and U4 supplied by the four channels. These voltages correspond to four different sampling times defined by the four lags t1, t2, t3 and t4 counted from the oscillator pulse T. In FIG. 3, these lags are respectively 30, 40, 50 and 60 $\mu$s.

Figure 3E:
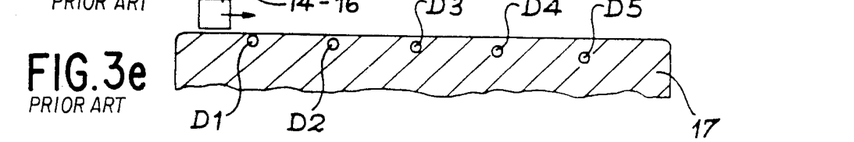

Line (e) in FIG. 3 shows the probe 14–16 in front of part 17 assumed to have five faults D1 to D5, located respectively at a depth of 0.5, 1.1, 2.2, 3.3 and 4.5 mm from the surface of the part.

When the probe passes over a fault, the sampled voltage starts to rise, then passes through a maximum, drops, is cancelled out, changes sign, passes through a minimum, rises again and is finally cancelled out.

Although satisfactory in certain respects, these apparatus suffer from disadvantages. Firstly the examination of the curves like those in FIG. 3 (or like those in FIG. 2, line (c)) is far from easy and it is difficult for the operator to obtain information of an accurate nature therefrom concerning the faults in the part. The theory of eddy currents is so complex in the case of saturated ferromagnetic parts (due to non-linear phenomena), that it is illusory to expect assistance therefrom.

Secondly, the prior art apparatuses do not make it possible to obtain freedom from certain signals appearing in the vicinity of welded parts, or joined plates, or any variation inherent in the geometry or structure of the examined part (background noise, transition, etc.).

These signals do not reveal the presence of a fault or defect and can instead mask lower amplitude signals, which in fact reveal a true defect.

Finally, these apparatuses suffer from balancing problems, which it is difficult to correct in the measure that the operation is of the pulse type and involves rapid transients. In the case of control by sinusoidal currents, it is possible to produce a correction signal having the frequency of the excitation signal and adjust the phase and amplitude of said signal in order to compensate the unbalance of the probe. However, in pulsed operation, said procedure is unsuitable due to the extensive spectrum of the signal to be corrected. The unbalance of the probe is not the same at every frequency and the correction signal cannot be reduced to a sinusoidal signal.

The present invention aims at obviating all these disadvantages.

To this end, the invention has as its first object a process for facilitating the analysis of sampled signals. The invention provides a process characterized in that representation takes place in a display plane of a point having a first coordinate along a first axis equal to a first sampled and held amplitude obtained for a short sampling delay and a second coordinate along a second axis equal to a second sampled and held amplitude obtained for a longer sampling delay. This point contains the information on the state of the part positioned facing the probe.

Thus, according to the invention only one pulse is required. However, in the aforementioned process of U.S. Pat. 4,084,136, it is necessary to have a recurrent sequence of square-wave pulses to obtain an information. Moreover, the shape and duration of all these pulses necessarily devolves from the recurrent sequence (e.g. the time will be T/8 if T is the recurrence period). In the invention, essentially a single pulse is formed, whose shape and duration are predetermined.

Naturally, if it is a question of controlling or inspecting an extensive area of a part, the probe or part will be moved and a pulse will be reemitted and so on. However, the time interval between the various pulses emitted will in no way influence the shape and duration of the excitation pulse.

In the case of a displacement and repetition of the excitation pulse, the display point will move if the probe passes over a defect and then the line of said point can be followed in the plane. The amplitude and phase of said line give information on the defects of the part along the inspected zone.

In such a process, when a differential probe travels along the part to be inspected and passes over a defect, the displayed point represents a figure of eight for reasons which will become more apparent hereinafter. This shape is very simple to analyze.

This shape does have a certain similarity with the curves obtained in the aforementioned sinusoidal current procedure. However, it must be stressed that there is an important difference between the two procedures making this similarity of a purely formal nature. In the sinusoidal current method, the measuring voltage is represented in an impedance plane. For this purpose, on one axis is plotted the resistive part of the impedance of the probe (in other words the measuring voltage part in phase with the exciting voltage) and on the perpendicular axis the reactive part of said impedance (in other words the part of the measuring voltage which is in quadrature with the exciting voltage). In the present invention, there is no question of an impedance plane, or of resistive or reactive components. It is a question of a plane having no particular electrical significance, but having unexpected properties with regards to the exploitation of the results. These properties are due to the face that one of the two sampling operations takes place at the start of the measuring pulse and the other at the end (in other words the sampling delay is respectively short and long).

Optionally, as in the sinusoidal eddy current method, before following the trace of the end of the vector, a rotation of the system of axes takes place making it possible to produce new components having properties not possessed by the two sampled signals and in particular the projection of the "background noise" on an axis. Moreover, in certain special cases, the use of non-perpendicular coordinate axes makes it possible to reveal more significant signal characteristics than those obtained by a representation along two perpendicular axes.

According to an advantageous variant of the inventive process each measuring pulse is sampled in several pairs of instants in order to obtain several pairs of sampled and held amplitudes and each of these pairs is represented in the same number of planes to obtain the same number of lines.

This treatment in several planes makes it possible, by comparison of the different responses in the different planes, to validate the interpretation. There must be correlation between the interpretations based on the different planes, otherwise an error in the hypotheses is detected (e.g. existence of a multiple defect, whereas the interpretation laws assume that only one defect is seen at once). Moreover, said treatment in several planes makes it possible to get round the disadvantages referred to hereinbefore with respect to the existence of undesirable parameters. To this end, the invention also provides for an elimination treatment of an undesirable parameter consisting of modifying the amplitude and-/or phase of a first line corresponding to a first pair of amplitudes and/or modifying the amplitude and/or phase of a second line corresponding to a second pair of amplitudes for obtaining two lines identical in phase and amplitude in an area corresponding to the undesired parameter and subtracting the modified amplitudes from the first pair from the modified amplitudes of the second pair, to obtain new components and a new line free from the undesired parameter.

Another object of the invention is a process like that defined hereinbefore, in which a balancing operation is also carried out. For this purpose, the measuring pulse supplied by the probe when it is located in front of an area assumed to be defect-free is recorded once and for all, this pulse constituting a reference pulse and said reference pulse is restored in synchronism with the measuring pulse obtained when the probe faces an area to be inspected and the thus restored reference pulse is subtracted from the measuring pulse.

Preferably, the reference pulse is digitally recorded by analog-digital conversion and is then read into a memory and the reference pulse is restored by reading the memory and digital-analog conversion.

Another object of the invention is a process as defined hereinbefore, in which the sample taken is compensated. For this purpose the sampled and held amplitude obtained when the probe faces an area considered to be defect-free is recorded once and for all, said amplitude constituting a compensation amplitude and the recorded compensation amplitude is subtracted from the measuring signal obtained when the probe is in front of an area to be inspected.

Another object of the invention is a pulsed eddy current control apparatus performing the process described hereinbefore.

In its most general structure, the apparatus is characterized in that it comprises means for displaying in a plane a point having a first coordinate on a first axis equal to a first sampled and held amplitude obtained with a short sampling delay and a second coordinate along a second axis equal to a second sampled and held amplitude obtained with a longer sampling delay.

Preferably, the probe and part are in relative displacement and the generator periodically reemits the exciting pulse, which makes it possible to obtain a curve representing the positional variations of the point in the display plane.

Preferably, the display means is constituted by a cathode ray oscilloscope, whose screen constitutes the representation plane, with a first horizontal axis and a second vertical axis.

In embodiments of the invention, said apparatus comprises means for eliminating undesirable parameters and/or balancing means for the probe and/or compensation means.

The invention is described in greater detail hereafter relative to non-limitative embodiments and the attached drawings, and wherein show.

In the following description, it is assumed that the probe moves with respect to a fixed part. However, it is obvious that it would be equivalent for the probe to be fixed and for the part to be inspected to be moved. The scope of the invention is not limited in this connection.

Figure 4:
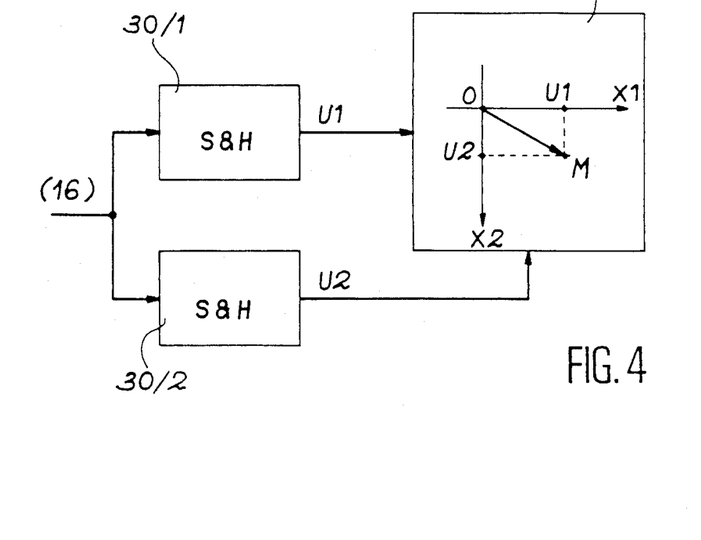
FIG. 4: The principle of the invention.

FIG. 4 illustrates the principle of the representation and exploitation of the signals according to the invention. The input of two channels 30/1 and 30/2 is connected to the measuring winding 16 of the probe, whilst their output supplies a signal corresponding to a sampling of the measuring signal. The sampling instants or times are respectively defined by a short time lag or delay and a long time lag or delay (in the already described FIG. 2 these lags are designated t1 and t3, t1 being short and t3 long). The concepts of short and long are very relative and are dependent on the shape of the current pulse and the depth at which it is wished to detect defects. Without this constituting a general rule, "short" can correspond to a point of the first alternative of the signal shown in FIG. 10 and "long" can relate to a subsequent alternation.

Voltage U1 and U2 are shown in a plane P defined by two axes OX1, OX2, signal U1 being plotted on axis OX1 and signal U2 on axis OX2.

Thus, a point M is defined, whose coordinates on axes OX1 and OX2 are quantities U1 and U2 or and this amounts to the same thing, a vector $\overrightarrow{OM}$, whose components are $\overrightarrow{OU1}$ and $\overrightarrow{OU2}$.

Figure 5:
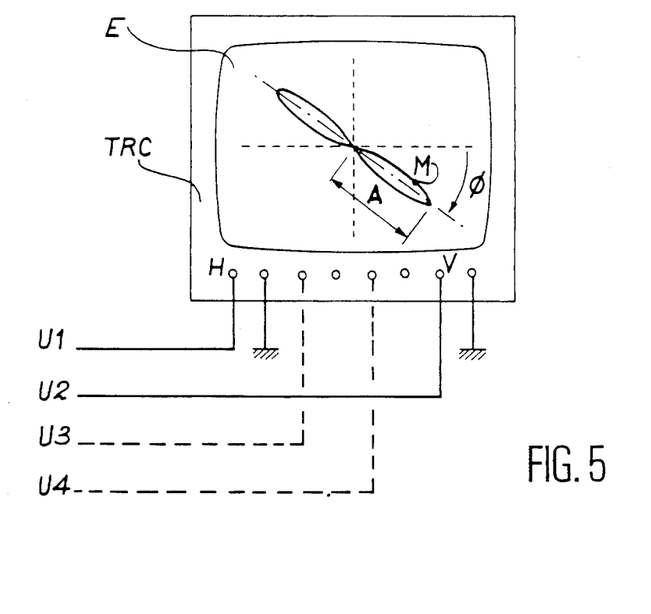
FIG. 5: A line obtained according to the invention when the probe passes in front of a fault or defect.

In practice, plane P is that of a recorder or the screen of an oscilloscope. The latter case is illustrated in FIG. 5, where the screen is designated E. A cathode ray tube TRC receives on a terminal H, connected to horizontal deflection plates, the voltage U1 and on a terminal V, connected to vertical deflection plates, the voltage U2.

When the probe moves along the part to be inspected, voltages U1 and U2 remain constant if the part is faultless and point M remains fixed in the plane. When the probe sweeps a defective area, point M (U1, U2) moves on screen E, where it plots a figure of eight with two substantially symmetrical lobes, if the probe or sensor used is of a differential nature. It is possible to define an amplitude A and a phase $\phi$ for said figure. The amplitude translates the "size" of the eight and the phase the orientation with respect to the horizontal axis.

Figures 6A, 6B:
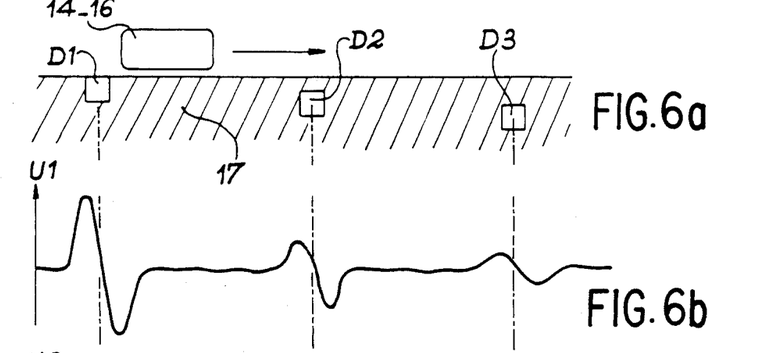
FIGS. 6a–6c: The configuration of two signals obtained according to the prior art in the case of three defects located at different depths.
Figure 6C:
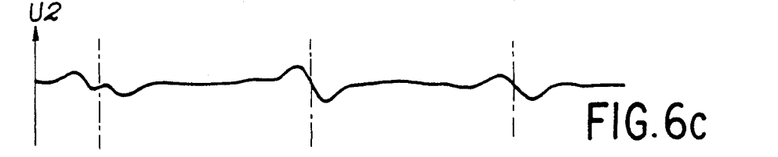
Figure 7:
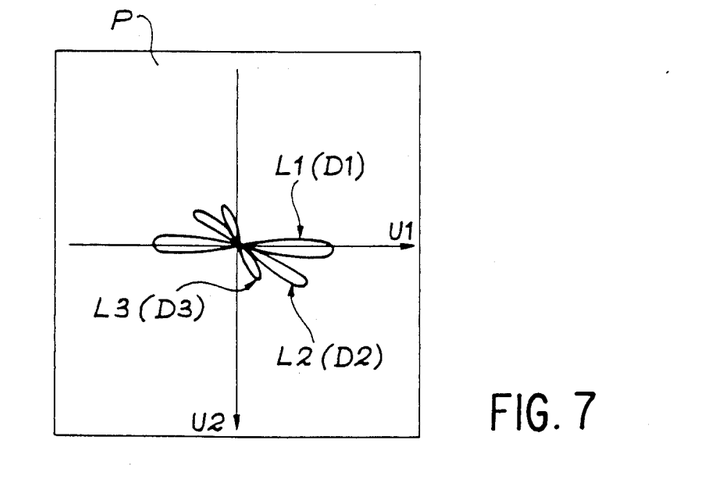
FIG. 7: The configuration of curves corresponding to the preceding case, but obtained according to the invention.

The reason for obtaining a figure of eight, which is somewhat surprising, in view of the fact that the components used have no link with resistive and reactive components like those encountered in conventional sinusoidal excitation methods, can be explained with the aid of FIGS. 6 and 7.

In FIG. 6, it is possible to see a probe 14–16 moving along a part 17 having three defects, namely one defect D1 close to the surface, a deeper defect D2 and a deep defect D3.

When the probe moves over these defects, the voltage U1, characterizing the sample taken with a short lag, has the configuration of line (b). Voltage U2, characterizing the sample taken with a long lag, has the configuration of FIG. (c). These curves are in accordance with the prior art, as illustrated in FIG. 2. However, in a representation plane according to the invention, the line obtained shows three lobes L1, L2 and L3 of different phases and amplitudes (FIG. 7). One lobe L1 is located on the horizontal axis and corresponds to defect D1. Thus, as said defect is close to the surface, it more particularly disturbs the start of the current pulse and only slightly disturbs its end. Therefore the "horizontal" component U1 preponderates, the "vertical" component U2 remaining weak. Lobe L1 consequently represents a weak phase.

The situation is reversed for defect D3, which is deep. In this case the end of the current pulse is disturbed, the start of the pulse only being slightly affected. Therefore it is the vertical component U2 which preponderates. Therefore lobe L3 has a phase close to 90°.

An intermediate situation exists for defect D2. The start and finish of the current pulse are disturbed by the defect and components U1 and U2 are of the same order, lobe L2 being inclined with a phase close to 45°.

Thus, the reading of the depth information of the defect is immediate according to the present invention and it is merely necessary to observe the phase of the figure obtained. The amplitude of the lobes also very clearly reveals the magnitude of the defect.

Apart from this advantage associated with the high degree of legibility of the results obtained, the invention provides a further advantage. It has been found that the configuration of the line represented according to the invention is identical to that obtained in the case of a control or inspection by sinusoidal eddy currents, so that it is possible to utilize the method of eliminating undesirable parameters known in connection with the latter inspection type.

Figure 8:
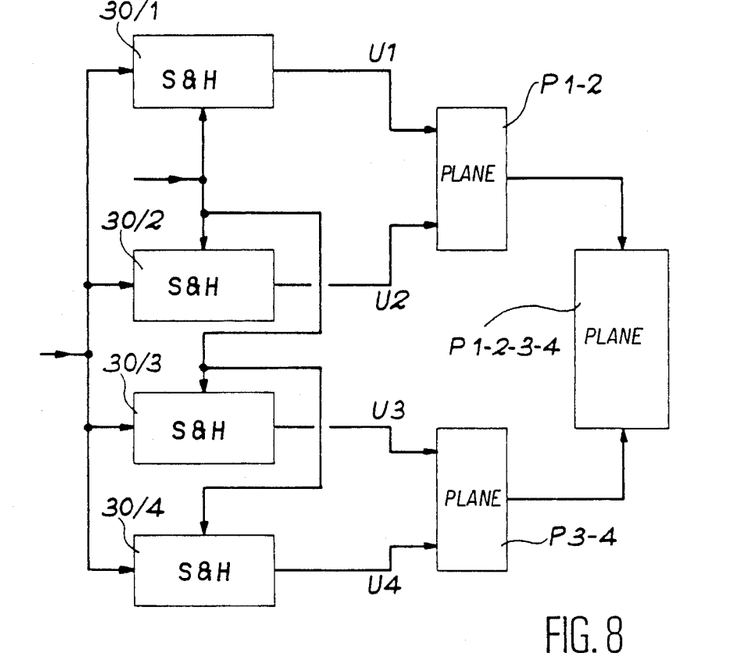
FIG. 8: The principle of combining results obtained in two different representation planes for eliminating an undesirable parameter.

This method is described in U.S. Pat. No. 4,061,968. This is diagrammatically shown in FIG. 8, where there is a plane P1-2 for the exploitation of two signals U1 and U2 supplied by two sample and hold circuits 30/1 and 30/2 and a plane P3-4 for the exploitation of two signals U3 and U4 supplied by two sample and hole circuit 30/3 and 30/4. The magnitudes shown in planes P1-2 and P3-4 are combined in amplitude and phase to give a new representation in a plant P1-2-3-4. In this plane, new magnitudes U'1 and U'2 are obtained, which are free from any undesirable parameter.

Figure 9:
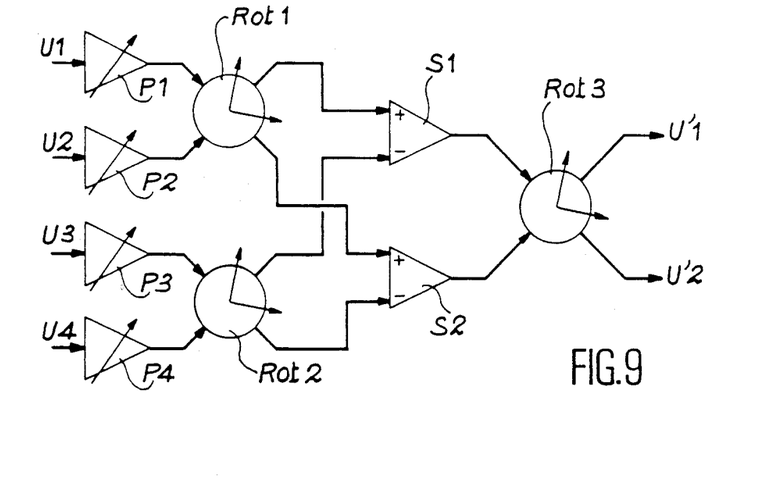
FIG. 9: An example of means for carrying out the aforementioned combination.

FIG. 9 illustrates the means for carrying out such a treatment of voltages U1, U2, U3 and U4. U1 and U2 are weighted by a factor k1, k2 using weighting means P1, P2 (which are in practice regulatable attenuators). Voltages k1U1 and k2U2 are transformed by a rotator Rot1 by an operation equivalent to a phase rotation Q1,2 (in practice in the form of quantities: $k1U1\cos\phi1,2 + k2U2\sin\phi1,2$ and $k1U1\sin\phi1,2 - k2U2\cos\phi1,2$.

Similar treatments are carried out on another pair of voltages U3 and U4 by means of weighting means P3, P4 and a rotator Rot2. The modified components are subtracted in pairs in two differential adders S1 and S2. A final rotator Rot3 makes it possible to rotate in its plane the figure which is finally obtained, if this is necessary.

Naturally, in certain cases, weighting coefficients could be taken equal to unity and certain rotations could be avoided.

It is possible in this way to act on the amplitude of one line (leaving its phase unchanged) and on the phase of the other line (leaving its amplitude unchanged), or to act only on one line (in amplitude and phase), whilst leaving the other unchanged.

Apart from the advantages associated with the treatment described hereinbefore, the invention leads to other advantages due to arrangements relating to the balancing and compensation of the measuring signal. As stated hereinbefore, the difficulty of balancing a pulsed current device is due to the width of the spectrum of the signals.

Figure 10:
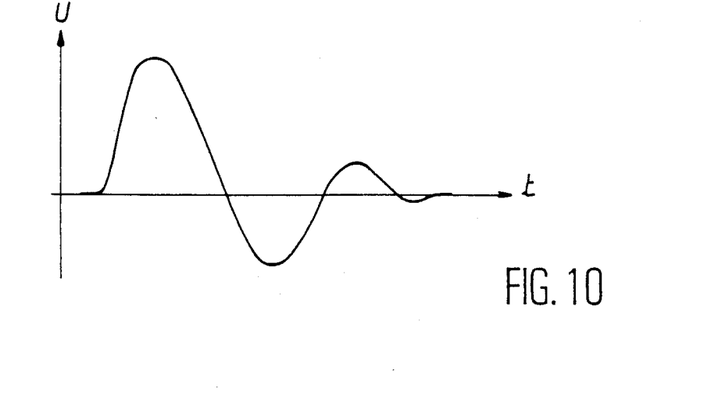
FIG. 10: The configuration of a signal supplied by a probe in the absence of a defect in the examined part.

FIG. 10 e.g. shows the configuration of the signal supplied by a probe when the latter faces a defect-free zone. Such a signal can be observed on the oscilloscope screen. A probe supplying such a signal, when the inspected part is defect-free, is either an absolute measuring probe, or a differential probe, whose construction symmetry is not adequate, which is virtually always the case.

Figure 11:
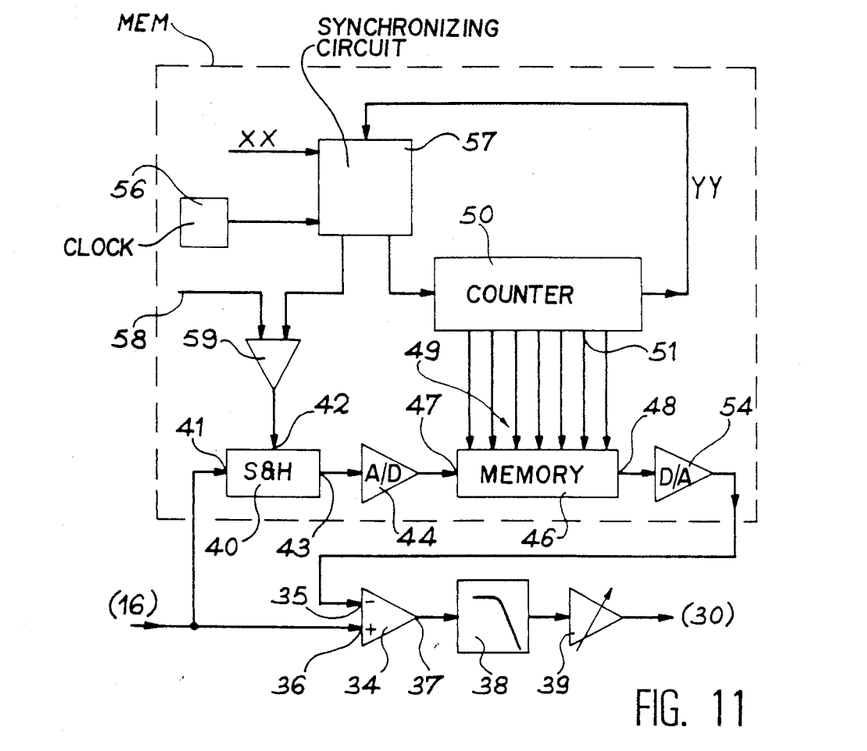
FIG. 11: Signal balancing means.

Thus, the apparatus according to the invention advantageously comprises balancing means, whereof one embodiment is shown in FIG. 11. It is possible to see a storage means MEM able to receive the measuring signal supplied by the probe, when the latter is in front of a faultless zone, an adder 34 with two inputs, one being negative 35 and connected to the output of the storage means, the other positive 36 being connected to the probe when the latter faces a zone to be inspected. Adder 34 is connected to a low-pass filter 38 followed by a variable gain amplifier 39.

In the illustrated embodiment, the storage means MEM comprises: a sample and hold circuit 40 having a signal input 41 connected to the probe and control input 42 receiving a balancing control signal and an output 43, an analog-digital converter 44 connected to the sample and hold circuit output 43, a memory 46 having a data input and output 47, 48 and an addressing input 49, the data input 47 being connected to the analog-digital converter 44, a counter having a digital output 51 connected to the addressing input 49 of the memory 46, a digital-analog converter 54 connected to the data output 48 of memory 46, a clock 56 controlling sample and hold circuit 40 and counter 50 through a circuit 57 located between clock 56 and counter 50 in such a way that the restored signal received by the negative input 35 of adder 34 is synchronous with the measuring pulse received by the positive input 36 of adder 34. Counting is started by control XX, whilst stopping and resetting is brought about by output YY of counter 50, when the entire wave shape contained in memory 46 has been swept.

Clock 56 e.g. functions at 10 MHz. The balancing control can be made operative by a control signal obtained by a connection 58 connected to an input of an amplifier 59, whereof another input receives clock pulses synchronized by circuit 57 and whose output is connected to the control input 42 of sample and hold circuit 40.

Memory 46 is of the RAM type and can have a capacity of 1 Kbyte. The counter 50 then has a maximum content of 1000. The sample and hold circuit 40 is fast, with a sample taking time of approximately 50 ns. Converter 44 is also fast (20 to 30 ns).

When perfect balancing of the measuring curve is not necessary, it may be sufficient to correct the measuring signal at a particular point, which is the sampling point, or at several points. In this case, the means of FIG. 11 are unnecessarily complex and it is merely necessary to use the means according to FIG. 12.

Figure 12:
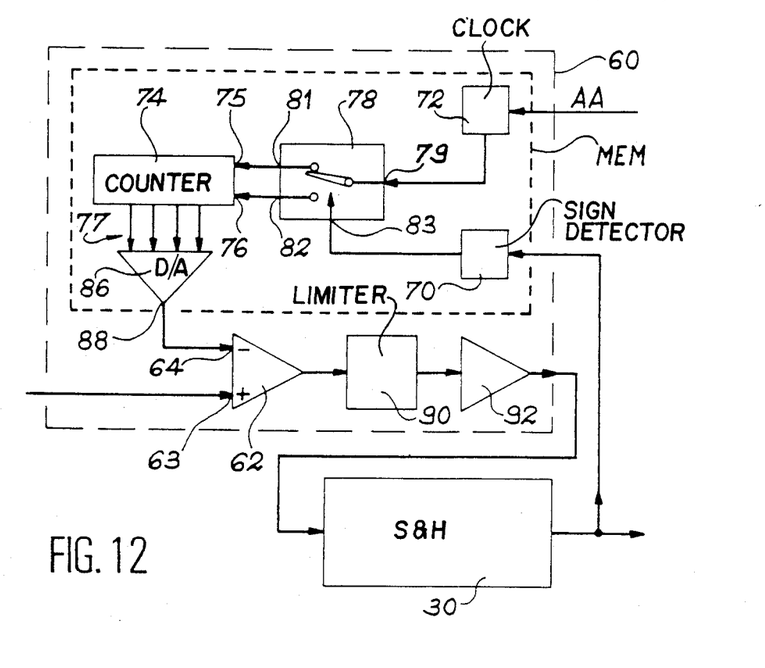
FIG. 12: Means for compensating the sampled voltage.

FIG. 12 shows a compensating circuit 60 placed in front of each sample and hold channel 30 (30/1, etc.). Circuit 60 comprises an adder 62 with two inputs, one being positive 63 and the other negative 64, a means MEM for storing a voltage connected to the negative input 64 of adder 62, said voltage being such that when the probe faces a defect-free zone, the output voltage of channel 30 is zero.

According to the illustrated variant, the storage means MEM comprises: a sign detector 70 connected to the output of channel 30, a clock 72, whose operation is activated by a balancing control signal, AA, a reversible counter 74 having a counting up input 75 and a counting down input 76, as well as a data output 77, a switch 78 having an input 79 connected to clock 72 and two outputs 81, 82 connected to inputs 75, 76 of counter 74 and a control input 83 connected to sign detector 70, a digital-analog converter 86 having an input connected to the data output 77 of counter 74 and an output 88 connected to the negative input 64 of comparator 62.

The apparatus is completed by a non-saturatable limiter 90 and an amplifier 92. The limiter limits the excursion of the signal in order to permit the correct operation of amplifier 92.

This circuit operates in the following way during the balancing phase caused by control AA. When the output signal of the channel is not zero, there is an increase or decrease to the content of reversible counter 74. The correcting signal applied to the negative input 64 of the adder is modified in the same sense, which has the effect of bringing the output voltage towards zero. When this state is obtained, the sample supplied by channel 30, for the sampling time of said channel, is zero, which corresponds to a compensated apparatus, because the probe is assumed to be facing a defect-free zone.

When control AA is stopped, the content of counter 72 is retained for all the subsequent measurements. Thus, the signal supplied at 30 truly reflects the influence of defect to the right of the probe.

The apparatus according to FIG. 12 must equip each of the processing or treatment channels, each time lag leading to a different voltage value to be compensated. Such a compensating circuit is economical and permits an improvement to the signal-to-noise ratio at the output of the apparatus, because by removing the continuous component of the signal supplied at 62, it permits an amplification at 92, prior to carrying out the sample and hold operation at 30. However, the improvement is not as great as with the variant involving the balancing of the complete curve, because the signal derivative is not cancelled out as is the case in 37.

In the pulsed eddy current non-destructive testing method, there is only an interest in precise points of the curve representing the measuring signal. These points are designated following observation of modifications to the complete curve.

Theory establishes that the curves representing amplitude-time signals, like that of FIG. 10, pass through fixed points when the probe-part distance varies and it is of interest to adopt these.

A sampler stage such as 30/1 in FIG. 1 consequently samples the value for a precise delay following the release of the current pulse. The investigation of a fixed point necessitates a quasi-continuous adjustment of this delay, which involves an analog delay circuit system. This constitutes a delicate point in this method, because a very high stability is required. A numerical delay by pulse counting would require a clock with a speed such that the circuits would become very complex and their operation might disturb the analog chain. The sample and hold circuit must respond in a very precise manner to the control and must consequently be very fast.

Moreover, the repetition of the measurement is such that the stored value must be retained for a sufficiently long time compared with the speed of said sample and hold circuit. However, this property would require a slow sampling. This difficulty is removed in the invention through a double sampling system illustrated in FIG. 13.

Figure 13:
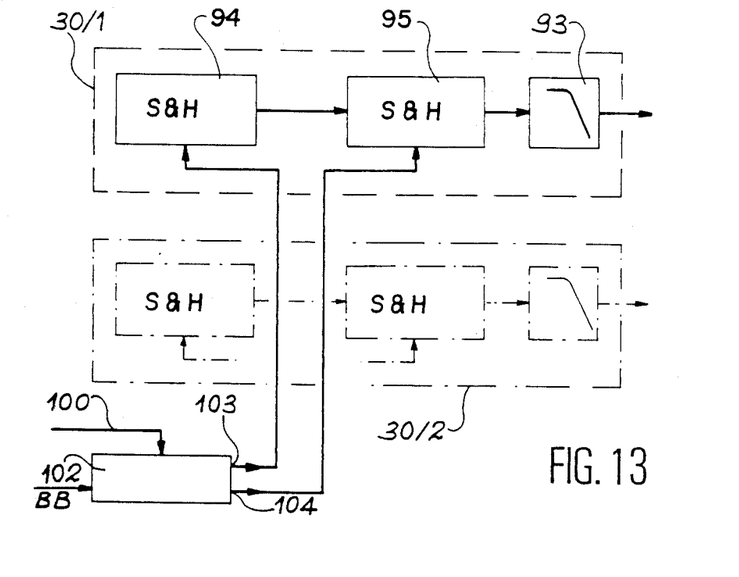
FIG. 13: A double sample and hold circuit.

Each sample and hold channel 30/1, etc. comprises a first sample and hold circuit 94 able to rapidly carry out (in less than 50 ns) the sampling operation, but which is only able to hold the sample for a limited time, as well as a second sample and hold circuit 95 connected to the first and able to slowly resample, with a fixed lag, the signal supplied by the first, but able to hold said resampled signal for a long time corresponding to the period of the exciting pulses. The latter can be 10 ms, when the recurrence frequency drops to 100 Hz.

A sampling control pulse BB from generator 10 is applied to circuit 102, which delays it in proportion to an analog control 100 and supplies at an output 103 a control pulse for the sample and hold circuit 90 and at an output 104 a delayed pulse addressed to the sample and hold circuit 92, delayed by a fixed value compared with that emitted at 103.

Thus, a sampled curved in staircase form is obtained, i.e. without noise when the mean derivative is zero. If appropriate, a low-pass filter 93 makes it possible to smooth the transients leading to disturbing stairs.

We claim:

1. A process for testing parts for defects by pulsed eddy currents comprising the steps of:
   providing a probe having first and second coils in the vicinity of the part and supplying said first coil with at least one exciting pulse having a given shape and duration;
   measuring a corresponding pulse on said second coil of said probe;
   sampling the measured pulse a plurality of times and holding the amplitude of the samples obtained;
   wherein a first sample of the measured pulse is sampled at a first instant having a short lag compared with the start of the corresponding pulse and said first sample is held, and a second sample of the measured pulse is sampled at a second instant having a longer lag compared with the start of the corresponding pulse and said second sample is held;
   displaying on a planar display means a point having a first coordinate on a first axis of a plane equal to the first sample held and having a second coordinate on a second axis of the plane equal to the second sample held, the position of said point indicating whether the part is defective.

2. A process according to claim 1, further comprising the steps of:
   relatively displacing the probe and the part;
   reemiting the exciting pulse; and
   displaying the corresponding point for each pulse;
   whereby all the points obtained provide a line whose amplitude and phase give an image of the part along the displacement zone.

3. A process according to claims 1 or 2, further comprising the steps of:
   sampling each measured pulse in several pairs of instants with short and long lags, in order to obtain several pairs of sampled and held amplitudes; and
   representing each of these pairs by a point in order to obtain the same number of points and the same number of lines.

4. A process according to claim 3, further comprising the steps of:
   eliminating an undesirable parameter by modifying the amplitude and/or phase of a first line corresponding to a first pair of amplitudes and/or modifying the amplitude and/or phase of a second line corresponding to a second pair of amplitudes;
   obtaining two lines which are identical in phase and amplitude in an area corresponding to the undesirable parameter; and
   subtracting the modified amplitudes of the first pair from the modified amplitudes of the second pair to obtain a new line free from the undesired parameter.

5. The process according to claim 1, wherein the sample and hold operation takes place on a previously balanced pulse obtained by: recording the measured pulse supplied by the probe when it faces an area considered to be defect-free, said pulse constituting a reference pulse and restoring said reference ulse in a synchronous manner with the measured pulse obtained when the probe faces an area to be inspected and subtracting the thus restored reference pulse from the measured pulse.

6. A process according to claim 5, further comprising the steps of:
registering digitally the reference pulse by analog-digital conversion;
storing the converted pulse in a memory; and
restoring a reference pulse by reading it out of memory and subjecting it to digital-analog conversion.

7. A process according to claim 1, further comprising the steps of:
measuring the variations of the sampled and held amplitude on a compensated measuring signal obtained by recording the sampled and held amplitude obtained when the probe faces an area considered to be defect-free, said amplitude constituting a compensating signal; and
subtracting the compensating signal from the measurement signal obtained when the probe is in front of an area to be inspected.

8. A process according to claim 7, wherein the recording takes place digitally and comprising the steps of:
sampling the measuring signal when the probe faces an area considered to be defect-free;
detecting the sign of the sample obtained;
controlling the counting up or down of the clock pulses in a counter as a function of said sign;
analog converting the result of the count;
subtracting the converted analog signal from the measurement signal; and
stopping counting up and down when the signal obtained after subtraction is zero, the final result of the count obtained constituting the recorded digital value of the compensating signal.

9. Pulsed eddy current testing apparatus comprising:
a probe having first and second coils positioned facing a part to be inspected,
a generator for emitting at least one pulse of predetermined shape and duration, said pulse being applied to said first coil of said probe,
at least two sample and hold channels having an input connected to said second coil of said probe, said channels sampling a measuring pulse at different instants designated by a time lag counted from the start of the measuring pulse supplied by the probe and holding the sampled amplitude,
means for displaying a point having for the first coordinate on a first axis one of the sampled and held amplitudes obtained with a short sampling lag and as the second coordinate along a second axis a second sample and held amplitude obtained with a long sampling lag.

10. Apparatus according to claim 9, further comprising:
means for relatively displacing the probe and the part,
wherein the generator then emits a sequence of recurring pulses having a recurrence period determined by the displacement speed, the displayed point then describes a line in the display plane, the amplitude and phase of said line giving information on the defects of the part along the displacement zone.

11. Apparatus according to claim 10, further comprising weighting means (P1, P2) and/or a rotator (Rot1) for modifying the amplitude and/or phase of a first line corresponding to a first pair of sampled and held amplitudes (U1, U2) and weighting means (P3, P4) and/or a rotator (Rot2) for modifying the amplitude and/or the phase of a second line corresponding to a second pair of sampled and held amplitudes (U3, U4) for obtaining two lines which are identical in amplitude and phase relative to an undesired parameter and subtractors (S1, S2) for subtracting pairwise the components of two vectors whose components have thus been modified to obtain a new line free from the undesired parameter.

12. Apparatus according to claim 9, further comprising balancing means having a device for recording the measuring signal supplied by the probe when the latter is in front of an area considered to be defect-free, an adder (34) with two inputs, the negative input (35) being connectable to the output of the recording device and the other positive input (36) being connected to the probe when the latter faces an area to be inspected and a means for controlling the recording device in synchronism with the measuring pulse.

13. Apparatus according to claim 12, wherein the recording device comprises:
a sample and hold circuit (40) having a signal input (41) connected to the probe and a control input (42) receiving a balancing control signal and an output (43),
an analog-digital converter (44) connected to the output (43) of the sample and hold circuit,
a memory (46) having a data input and output (47, 48) and an addressing input (49), the data input (47) being connected to the analog-digital converter (44),
a counter (50) having a digital output (51) connected to the addressing input (49) of the memory (46),
a digital-analog converter (54) connected to the data output (48) of memory (46),
a clock (56) controlling the sample and hold circuit (40) and counter (50),
a circuit (57) located between clock (56) and counter (50), so that the restored signal received by the negative input (35) of adder (34) is synchronous with the measuring pulse received by the positive input (36) of adder (34).

14. Apparatus according to claim 9, further comprising a compensating circuit (60) placed in front of each sample and hold channel (30), said circuit (60) incorporating an adder (62) with two inputs, the positive input being (63) and the negative input (64), as well as a means MEM for storing a voltage connected to the negative input (64) of adder (62), said voltage being such that when the probe is located in front of an area considered to be defect-free, the output voltage of channel (30) is zero.

15. Apparatus according to claim 14, wherein the storage means comprises:
a sign detector (70),
a clock (72),
a reversible counter (74) having a counting up input (75) and a counting down input (76), as well as a data output (77),
a switch (78) having an input (79) connected to clock (72) and two outputs (81, 82) connected to the inputs (75, 76) of counter (74) and a control input (83) connected to the sign detector (70),
a digital-analog converter (86) having an input connected to the data output (77) of counter (74) and an output (88) connected to the negative input (64) of comparator (62).

16. Apparatus according to claim 9, wherein each sample and hold channel (30/1, etc.) comprises a first sample and hold circuit (90) able to rapidly carry out sampling, but only able to hold the sample for a short time, and a second sample and hold circuit (92) connected to the first and able to slowly resample, with a fixed lag, the signal supplied by the first circuit, but able to hold said resampled signal for a long time.

* * * * *